(12) United States Patent
Rekoske et al.

(10) Patent No.: US 10,427,997 B2
(45) Date of Patent: Oct. 1, 2019

(54) MODULAR MEMBRANE SYSTEM AND METHOD FOR OLEFIN SEPARATION

(71) Applicant: UOP LLC, Des Plaines, IL (US)

(72) Inventors: James E. Rekoske, Glenview, IL (US); Trung Pham, Mount Prospect, IL (US); Stanley J. Frey, Palatine, IL (US); Chunqing Liu, Arlington Heights, IL (US)

(*) Notice: Subject to any disclaimer, the term of this patent is extended or adjusted under 35 U.S.C. 154(b) by 0 days.

(21) Appl. No.: 15/855,407

(22) Filed: Dec. 27, 2017

(65) Prior Publication Data

US 2019/0193021 A1 Jun. 27, 2019

(51) Int. Cl.
| | | |
|---|---|---|
| C07C 7/144 | (2006.01) |
| B01D 71/64 | (2006.01) |
| B01D 71/68 | (2006.01) |
| C07C 7/00 | (2006.01) |
| B01D 53/22 | (2006.01) |
| B01D 71/82 | (2006.01) |

(Continued)

(52) U.S. Cl.
CPC ............ *C07C 7/144* (2013.01); *B01D 53/226* (2013.01); *B01D 53/227* (2013.01); *B01D 53/228* (2013.01); *B01D 69/142* (2013.01); *B01D 71/70* (2013.01); *B01D 71/82* (2013.01); *C07C 7/005* (2013.01); *B01D 63/08* (2013.01); *B01D 67/0013* (2013.01); *B01D 69/02* (2013.01); *B01D 69/12* (2013.01); *B01D 69/148* (2013.01); *B01D 71/64* (2013.01); *B01D 71/68* (2013.01); *B01D 2256/24* (2013.01); *B01D 2257/306* (2013.01); *B01D 2257/553* (2013.01); *B01D 2257/7022* (2013.01); *B01D 2317/025* (2013.01); *B01D 2319/04* (2013.01); *B01D 2325/022* (2013.01); *B01D 2325/20* (2013.01); *B01D 2325/36* (2013.01)

(58) Field of Classification Search
CPC .......................... B01D 53/226; B01D 53/227
See application file for complete search history.

(56) References Cited

U.S. PATENT DOCUMENTS

| | | | |
|---|---|---|---|
| 3,133,132 A | 5/1964 | Sidney et al. | |
| 5,015,268 A * | 5/1991 | Ho ...................... | B01D 69/142 585/818 |

(Continued)

FOREIGN PATENT DOCUMENTS

| | | |
|---|---|---|
| CN | 103402614 A | 11/2013 |
| CN | 104275094 A | 1/2015 |

(Continued)

OTHER PUBLICATIONS

Chen, "Bioinspired fabrication of composite pervaporation membranes with high permeation flux and structural stability", Journal of Membrane Science 344 (2009) 136-143.

(Continued)

*Primary Examiner* — Philip Y Louie
*Assistant Examiner* — Alyssa L Cepluch

(57) ABSTRACT

A membrane process is provided for separating light olefins from light paraffins to produce a polymer grade light olefin product stream that is about 99.5 mol % ethylene or propylene. The process involves multiple stages to achieve the high purity product and provides for processing hydrocarbon streams that have differing concentrations of light olefins.

19 Claims, 4 Drawing Sheets

(51) Int. Cl.
B01D 71/70 (2006.01)
B01D 69/14 (2006.01)
B01D 69/02 (2006.01)
B01D 69/12 (2006.01)
B01D 63/08 (2006.01)
B01D 67/00 (2006.01)

(56) References Cited

U.S. PATENT DOCUMENTS

| | | | |
|---|---|---|---|
| 5,198,316 | A | 3/1993 | Wernet et al. |
| 5,256,295 | A | 10/1993 | Baker et al. |
| 5,670,051 | A | 9/1997 | Pinnau et al. |
| 6,830,691 | B2 * | 12/2004 | Colling ............ B01D 53/225 210/641 |
| 6,932,589 | B2 | 8/2005 | Suzuki |
| 7,048,846 | B2 | 5/2006 | White et al. |
| 7,125,935 | B2 | 10/2006 | Andrews et al. |
| 7,361,800 | B2 | 4/2008 | Herrera et al. |
| 7,803,275 | B2 | 9/2010 | Partridge et al. |
| 8,173,323 | B2 | 5/2012 | An et al. |
| 8,337,598 | B2 | 12/2012 | Yates et al. |
| 8,366,804 | B2 | 2/2013 | Liu et al. |
| 8,561,812 | B2 | 10/2013 | Liu et al. |
| 8,574,785 | B2 | 11/2013 | Kim et al. |
| 8,829,059 | B2 | 9/2014 | Wynn et al. |
| 8,912,288 | B2 | 12/2014 | Liu et al. |
| 9,017,451 | B2 | 4/2015 | Wynn et al. |
| 9,126,152 | B2 | 9/2015 | Liu et al. |
| 9,126,154 | B2 | 9/2015 | Liu et al. |
| 9,126,156 | B2 | 9/2015 | Liu et al. |
| 9,211,508 | B2 | 12/2015 | Liu et al. |
| 9,216,390 | B2 | 12/2015 | Ho et al. |
| 9,327,248 | B1 * | 5/2016 | Liskey ............ B01D 71/64 |
| 9,751,050 | B2 | 9/2017 | Zhou et al. |
| 10,258,929 | B2 | 4/2019 | Liu et al. |
| 2004/0154980 | A1 | 8/2004 | Kim et al. |
| 2004/0215045 | A1 | 10/2004 | Herrera et al. |
| 2006/0000778 | A1 | 1/2006 | Childs et al. |
| 2007/0190385 | A1 | 8/2007 | Lee et al. |
| 2008/0063917 | A1 | 3/2008 | Yamashita et al. |
| 2008/0268314 | A1 | 10/2008 | Han et al. |
| 2009/0277837 | A1 | 11/2009 | Liu et al. |
| 2010/0018926 | A1 | 1/2010 | Liu et al. |
| 2010/0147148 | A1 | 6/2010 | Rabiei |
| 2011/0094960 | A1 | 4/2011 | Zhou et al. |
| 2011/0316181 | A1 * | 12/2011 | Liu ............ B01D 53/228 264/45.5 |
| 2012/0031833 | A1 * | 2/2012 | Ho ............ B01D 67/0051 210/488 |
| 2012/0046512 | A1 * | 2/2012 | Gauthier ............ B01J 23/755 585/841 |
| 2012/0285881 | A1 | 11/2012 | Jikihara et al. |
| 2013/0255483 | A1 | 10/2013 | Sanders et al. |
| 2013/0299428 | A1 | 11/2013 | Bikel et al. |
| 2013/0233791 | A1 | 12/2013 | Koo et al. |
| 2014/0137734 | A1 | 5/2014 | Liu et al. |
| 2014/0290478 | A1 | 10/2014 | Liu et al. |
| 2015/0025293 | A1 | 1/2015 | Feiring et al. |
| 2015/0053079 | A1 | 2/2015 | Koros et al. |
| 2015/0068978 | A1 | 3/2015 | Lando et al. |
| 2015/0098872 | A1 | 4/2015 | Kelly et al. |
| 2015/0328594 | A1 * | 11/2015 | Liskey ............ B01D 53/228 528/337 |
| 2016/0107127 | A1 * | 4/2016 | Lee ............ B01D 69/125 96/4 |
| 2016/0158692 | A1 * | 6/2016 | Aoki ............ B01D 53/228 521/27 |
| 2016/0177035 | A1 | 6/2016 | Liu et al. |
| 2016/0325229 | A1 | 11/2016 | Zhou et al. |
| 2017/0291143 | A1 | 10/2017 | Zhou et al. |
| 2017/0354918 | A1 | 12/2017 | Liu et al. |
| 2018/0001277 | A1 | 1/2018 | Liu et al. |
| 2018/0154311 | A1 | 6/2018 | Zhou et al. |
| 2018/0333675 | A1 | 11/2018 | Liu et al. |
| 2018/0345230 | A1 | 12/2018 | Karns et al. |
| 2019/0060841 | A1 | 2/2019 | Liu et al. |

FOREIGN PATENT DOCUMENTS

| | | |
|---|---|---|
| EP | 458598 A2 | 11/1991 |
| EP | 1375459 A1 | 1/2004 |
| EP | 2545985 A1 | 1/2013 |
| EP | 2764908 A1 | 8/2014 |
| WO | 2009002747 A2 | 12/2008 |

OTHER PUBLICATIONS

Ma, "High-flux thin-film nanofibrous composite ultrafiltration membranes containing cellulose barrier layer", J. Mater. Chem., 2010, 20, 4692-4704 (2010).

Wanichapichart, Characteristics of polyethersulfone/chitosan composite membranes:, Biophysics Unit, Membrane Science and Technology Research Center, Faculty of Science, Prince of Songkia University, Had Yai, Songkhla, Thailand 90112. (2003).

Riley, "Thin-Film Composite Membrane for Single-Stage Seawater Desalination by Reverse Osmosis", Applied Polymer Symposium No. 22, pp. 255-267 (1973).

Hess et al., Prpene/prpane separation with copolyimide membranes containing silver ions, Journal of Membrane Science, vol. 275, issue 1-2, Apr. 20, 2006, pp. 52-60.

PCT Search Report dated Sep. 14, 2017 for PCT Application No. PCT/US2017/038294.

Kang, "Novel Application of Partially Positively Charged Silver Nanoparticles for Facilitated Transport in Olefin/Paraffin Separation Membranes", Chem. Mater. 2008, 20, 1308-1311.

PCT Search Report dated Oct. 5, 2017 for PCT Appl. No. PCT/US2017/038307.

PCT Search Report dated Aug. 30, 2018 for PCT Appl. No. PCT/US2018/032251.

PCT Search Report dated Sep. 14, 2017 for PCT Appl. No. PCT/US2017/036265.

Kudinov, "Separation Characteristics of an Ejector Membrane-Sorption Hybrid System", Theoretical Foundations of Chemical Engineering, 2014, vol. 48, No. 6, 832-836, Pleiades Publishing, Ltd., 2014.

PCT Search Report dated Aug. 30, 2018 for PCT Appl. No. PCT/US2018/035004.

PCT Search Report dated Nov. 29, 2018 for PCT Appl. No. PCT/US2018/047547.

* cited by examiner

MODULAR MEMBRANE SYSTEM AND METHOD FOR OLEFIN SEPARATION

BACKGROUND OF THE INVENTION

The invention relates to a process for using membrane systems to separate light olefins from paraffins without using distillation columns.

Separation of light olefins from paraffins is an energy intensive process. The current process involves traditional use of distillation columns which include 100-200 trays which make these columns among the tallest in a refinery or petrochemical complex.

Over 170 Separex™ membrane systems have been installed in the world for gas separation applications such as for the removal of acid gases from natural gas, in enhanced oil recovery, and hydrogen purification. Two new Separex™ membranes (Flux+ and Select) have been commercialized recently by Honeywell UOP, Des Plaines, Ill. for carbon dioxide removal from natural gas. These Separex™ spiral wound membrane systems currently hold the membrane market leadership for natural gas upgrading. These membranes, however, do not have outstanding performance for olefin/paraffin separations. Development of new stable and very high selectivity membranes is critical for the future success of membranes for olefin/paraffin separation applications such as propylene/propane and ethylene/ethane separations.

Light olefins, such as propylene and ethylene, are produced as co-products from a variety of feedstocks in a number of different processes in the chemical, petrochemical, and petroleum refining industries. Various petrochemical streams contain olefins and other saturated hydrocarbons. Typically, these streams are from stream cracking units (ethylene production), catalytic cracking units (motor gasoline production), or the dehydrogenation of paraffins.

Currently, the separation of olefin and paraffin components is performed by superfraction with very high reflux ratios, which is expensive and energy intensive due to the low relative volatilities of the components. Large capital expense and energy costs have created incentives for extensive research in this area of separations, and low energy-intensive membrane separations have been considered as an attractive alternative.

In principle, membrane-based technologies have the advantages of both low capital cost and high-energy efficiency compared to conventional separation methods for olefin/paraffin separations, such as propylene/propane and ethylene/ethane separations. Four main types of membranes have been reported for olefin/paraffin separations. These are facilitated transport membranes, polymer membranes, mixed matrix membranes, and inorganic membranes. Facilitated transport membranes, or ion exchange membranes, which sometimes use silver ions as a complexing agent, have very high olefin/paraffin separation selectivity. However, poor chemical stability, due to carrier poisoning or loss, high cost, and low flux, currently limit practical applications of facilitated transport membranes.

Separation of olefins from paraffins via conventional polymer membranes has not been commercially successful due to inadequate selectivities and permeabilities of the polymer membrane materials, as well as due to plasticization and contaminant issues. Polymers that are more permeable are generally less selective then are less permeable polymers. A general trade-off has existed between permeability and selectivity (the so-called "polymer upper bound limit") for all kinds of separations, including olefin/paraffin separations. In recent years, substantial research effort has been directed to overcoming the limits imposed by this upper bound. Various polymers and techniques have been used, but without much success in terms of improving the membrane selectivity.

More efforts have been undertaken to develop metal ion incorporated, high olefin/paraffin selectivity facilitated transport membranes. The high selectivity for olefin/paraffin separations is achieved by the incorporation of metal ions such as silver (I) or copper (I) cations into the solid nonporous polymer matrix layer on top of the highly porous membrane support layer (so-called "fixed site carrier facilitated transport membrane") or directly into the pores of the highly porous support membrane (so-called "supported liquid facilitated transport membrane") that results in the formation of a reversible metal cation complex with the pi bond of olefins, whereas no interaction occurs between the metal cations and the paraffins. Addition of water, plasticizer, or humidification of the olefin/paraffin feed streams to either the fixed site carrier facilitated transport membranes or the supported liquid facilitated transport membranes is usually required to obtain reasonable olefin permeances and high olefin/paraffin selectivities. The performance of fixed site carrier facilitated transport membranes is much more stable than that of the supported liquid facilitated transport membranes and the fixed site carrier facilitated transport membranes are less sensitive to the loss of metal cation carriers than the supported liquid facilitated transport membranes.

SUMMARY OF THE INVENTION

The invention involves a process to separate a hydrocarbon stream comprising a mixture of light olefins and light paraffins. The first step of the process is to pretreat the hydrocarbon stream to remove impurities to produce a treated hydrocarbon stream. Then the treated hydrocarbon stream is vaporized to produce a gaseous treated hydrocarbon stream and add liquid or vapor water. The gaseous treated hydrocarbon stream is sent to a first membrane module comprising a multiplicity of membrane units comprising membranes having a higher permeance and a lower selectivity than a second membrane module to produce a first permeate stream comprising a higher concentration of light olefins than the gaseous treated hydrocarbon stream and a first non-permeate stream comprising a higher concentration of light paraffins than the gaseous treated hydrocarbon stream. Then the first permeate stream is sent to the second membrane module comprising membrane units comprising membranes having a higher selectivity than the membranes in the first membrane module to produce a second permeate stream comprising at least 99% light olefins and a second non-permeate stream comprising a lower concentration of light olefins than the second permeate stream. The first non-permeate stream is sent to a third membrane module comprising membranes having a higher permeance and lower selectivity than the membranes in the second membrane module to produce a third permeate stream comprising a higher concentration of light olefin than the said non-permeate stream and a non-permeate stream comprising a majority concentration of paraffin. The third permeate stream is sent to a fourth membrane module comprising membrane units comprising membranes having a higher selectivity than the membranes in the first membrane units in the first membrane module to produce a fourth permeate stream comprising a higher concentration of light olefin than the third permeate stream. Then the fourth permeate stream can be combined with the first permeate stream. In addition, the second non-permeate stream can be combined with the third permeate stream.

In an embodiment of the invention, at least a portion of the hydrocarbon stream comprises a feed from a propane dehydrogenation reaction comprising about 30-40% propylene. The process comprises an initial rectification membrane module comprising membrane units having higher permeance and a lower selectivity than the membrane units in the second membrane module to produce a rectification permeate stream comprising about 55-80% light olefin. The rectification permeate stream is then sent to the first membrane module. In some embodiments of the invention the rectification permeate stream is mixed with the hydrocarbon stream before the hydrocarbon stream is sent to the first membrane module. The rectification membrane module may comprise membrane units comprising membranes as recently described in U.S. application Ser. No. 15/610,305 filed May 31, 2017; U.S. application Ser. No. 15/600,300 filed May 18, 2017; and U.S. application Ser. No. 15/599,258 filed May 18, 2017 incorporated herein in their entireties.

The product stream from the second permeate stream may comprise 99.3 to 99.9% propylene. The hydrocarbon stream that is used in this process may be from one or more processes selected from the group consisting of thermal steam crackers, fluid catalytic cracking and propane dehydrogenation. Water vapor is added to the stream that is being treated prior to passing through a membrane module. Accordingly, water vapor is added to the feed streams for said first membrane module, said second membrane module, said third membrane module, and said fourth membrane module before each of said feed streams enters the membrane module. The membranes used in the first membrane module, the third membrane module, and the rectification membrane module can be the same or different and can be selected from the membranes described in U.S. application Ser. No. 15/610,305 filed May 31, 2017; U.S. application Ser. No. 15/600,300 filed May 18, 2017; and U.S. application Ser. No. 15/599,258 filed May 18, 2017 incorporated herein in their entireties. The second membrane module and the fourth membrane module may comprise the same or similar functioning membranes that comprise a membrane as recently described in U.S. application Ser. No. 15/598,168 filed May 17, 2017; U.S. application Ser. No. 15/615,134 filed Jun. 6, 2017; and U.S. Provisional Application No. 62/549,820 filed Aug. 24, 2017 incorporated herein in their entireties.

Sufficient water vapor is added to each hydrocarbon stream before each stream contacts a membrane module so that the stream has from 10 to 100% humidity and more typically has from 60-90% humidity. The impurities that are removed from the hydrocarbon before being treated by the membrane system of the present invention include arsine, phosphine, sulfur compounds, dienes and acetylenes. The hydrocarbon stream is at a pressure from about 100 to 500 psig before entering a membrane module and is at a temperature from about 30 to 90° C. The main light olefins that are produced by the present invention are ethylene and propylene. The process that is described herein includes details for the production of propylene, but a similar process may take place to produce ethylene.

DETAILED DESCRIPTION OF THE INVENTION

Figure 1:
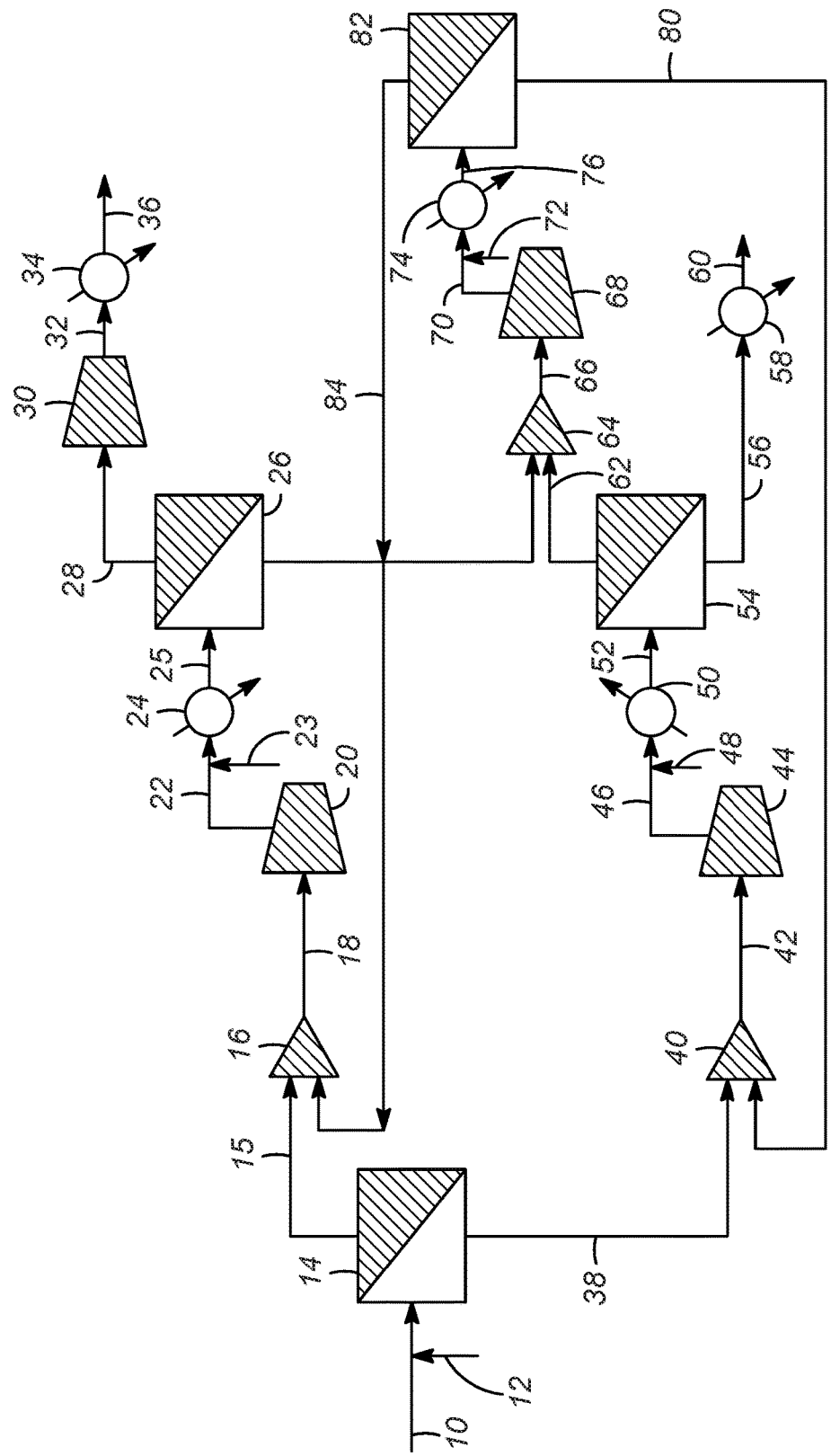
FIG. 1 is a modular flow scheme of the invention showing four membrane modules to produce a polymer grade propylene stream.

The overall process includes a pretreatment system followed by membrane separation. The pretreatment includes adsorption units to remove impurities such as arsine, phosphine, sulfur compounds including mercaptans and other impurities present in the feed. For MAPD (methylacetylene, propanediene), a customized catalyst system can selectively hydrogenate them to mono-olefins so they will not enter the membrane unit. The treated liquid feed is then vaporized and heated to 40-70° C., preferably 45-60° C. and added with water to 10-100% humidity, preferably 60-90% humidity before entering the membrane system. In one embodiment as shown in FIG. 1, a typical treated feed from a fluid catalytic cracking (FCC) unit (about 65 mol % propylene) enters the membrane system to produce about 40 thousand metric tons per year (KMTA) of a product that is 99.5 mol % propylene. In the examples discussed in this application, the membrane system consists of 4 membrane modules of 100, 60, 120 and 80 elements. The treated feed enters the first membrane module which has high propylene permeance (about 160-330 GPU, 1 GPU=$10^{-6}$ cm$^3$ (STP)/cm$^2$·sec·cmHg) and moderately low propylene/propane selectivity (about 30-50). The permeate propylene with a concentration of 70-95 mol % propylene, more often 75-90% propylene, is contacted with a second module membrane with high selectivity compared to the first module's selectivity (about 250-1100, or preferably 300-950), which produces a permeate of 99.3-99.9 mol % propylene, preferably 99.4-99.8 mol % propylene. The retentate from the first module with a concentration of propylene in the range of 12-25%, preferably 16-22%, is contacted with a third membrane module with high permeance (about 160-330 GPU), and low selectivity (about 30-50) to produce a propane rich product with low C3=concentration, 3-15%, preferably 5-10%. The permeate from the third membrane module is combined with the retentate of the second membrane module with C3=in the range of 30-50%, or preferably 35-45%, to contact with a fourth membrane module with high selectivity (about 250-1100, or preferably 300-950). The permeate from the fourth membrane module with 70-95% mol C3=, preferably 75-90%, is combined with the permeate from the first membrane module (and contacted with second membrane module aforementioned). The retentate from the fourth membrane module with 12-25% propylene, preferably 16-22% propylene, is combined with the retentate from the first membrane module with similar concentration of propylene and enters the third membrane module as described above. The first membrane module can be referred as first stage, second membrane module as second stage, third as third stage and fourth as fourth stage. There are interstage compression and cooling/heating exchangers included as shown in the drawings to reach the required operating pressure and temperature. Pressure range is 50-500 psig, or preferably 100-280 psig. Temperature range is 30-90° C., or preferably 35-65° C. The mixed streams should not be more than 10% different in composition to avoid system entropy increases and value loss by mixing relatively high purity streams with much less pure streams.

Figure 2:
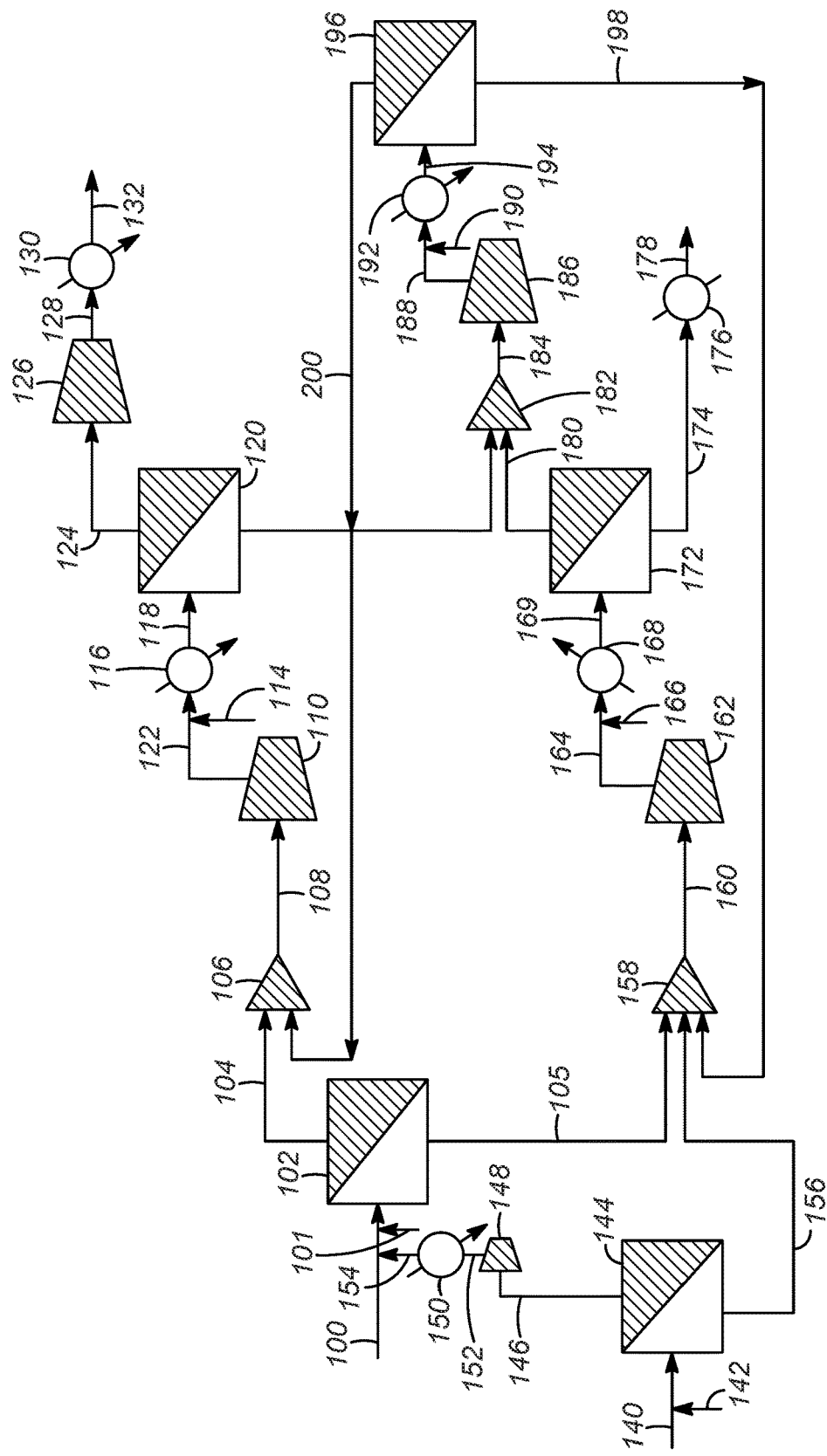
FIG. 2 is a modular flow scheme of the invention that shows the processing of two olefin-containing streams with different levels of light olefins.

In a second embodiment of the invention as shown in FIG. 2, water is added to a second treated feed from a propane dehydrogenation (PDH) unit (about 35% propylene) enters an additional membrane module for rectification to 55-80 mol % propylene, preferably 60-75 mol % propylene before joining the main membrane system described above for the FCC feed. The additional membrane module contains membranes that have a high permeance (about 160-330 GPU), and low selectivity (about 30-50), and can be referred as a rectification stage if the feed is secondary (PDH in addition to FCC main feed). The permeate from rectification stage is combined with the FCC feed to enter the first stage, and the retentate stream from the rectification stage with a propylene concentration of 15-25 mol %, preferably or more typically at about 16-22 mol %, is combined with the retentate from the first and fourth stage and then fed to the third stage. If there is an independent feed with 30-40 mol % propylene (from PDH), the rectification stage then becomes the first contacting stage, and other stages become sub-sequent 2nd, 3rd, 4th and 5th stage. Not specified herein, but in some embodiments of the invention, other untreated feeds can be combined and treated before entering the system.

The membranes used in the first membrane module, the third membrane module, and the rectification membrane module can be the same or different and can be selected from the membranes described in U.S. application Ser. No. 15/610,305 filed May 31, 2017; U.S. application Ser. No. 15/600,300 filed May 18, 2017; and U.S. application Ser. No. 15/599,258 filed May 18, 2017 incorporated herein in their entireties.

Some of the facilitated transport membranes described in U.S. application Ser. No. 15/610,305 can be used in the first membrane module, the third membrane module, and the rectification membrane module in the present invention, wherein said facilitated transport membrane may comprise a carboxylic acid functional group containing polyimide wherein the carboxylic acid functional groups are ion-exchanged or chelated with metal cations such as silver (I) or copper (I) cations. The metal cation ion-exchanged or chelated carboxylic acid functional group containing polyimide described in U.S. application Ser. No. 15/610,305 comprising a plurality of repeating units of formula (I)

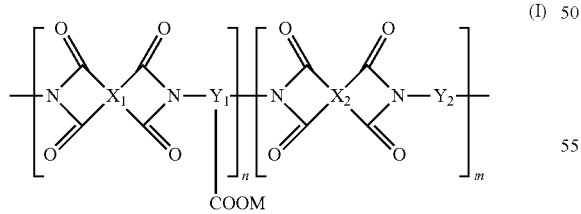

wherein $X_1$ and $X_2$ are selected from the group consisting of

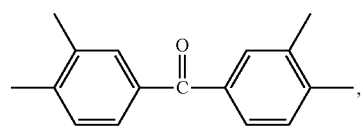

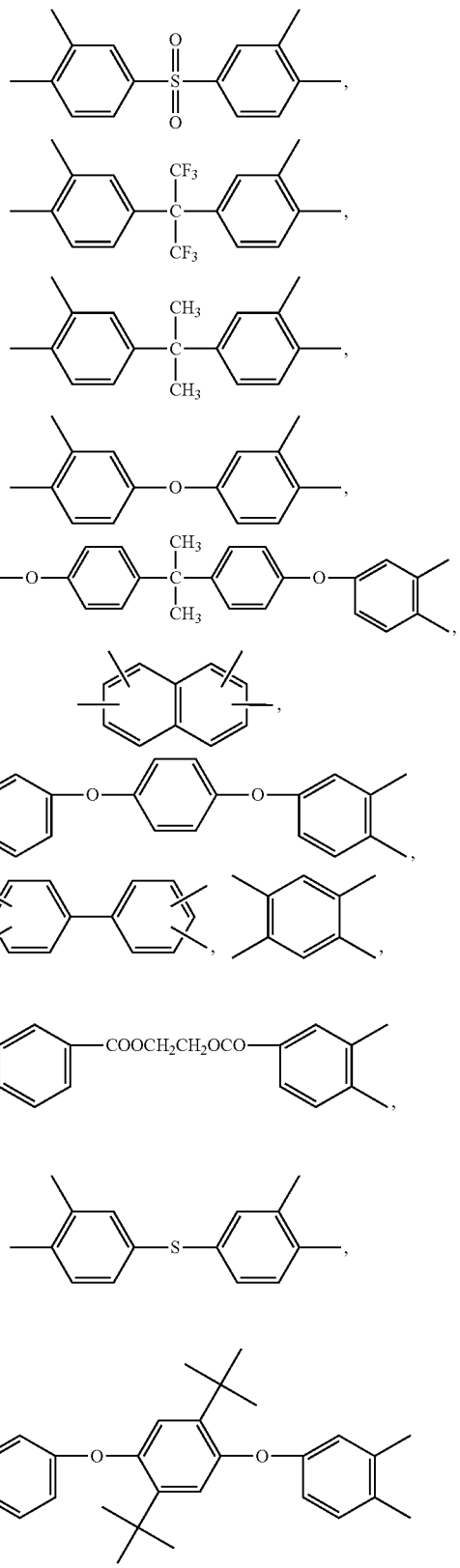

and mixtures thereof, and wherein X1 and X2 may be the same or different from each other; wherein $Y_1$—COOM is selected from the group consisting of

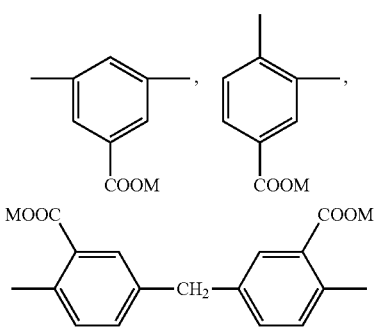

and mixtures thereof and wherein M is selected from silver (I) cation or copper (I) cation; wherein Y2 is selected from the group consisting of

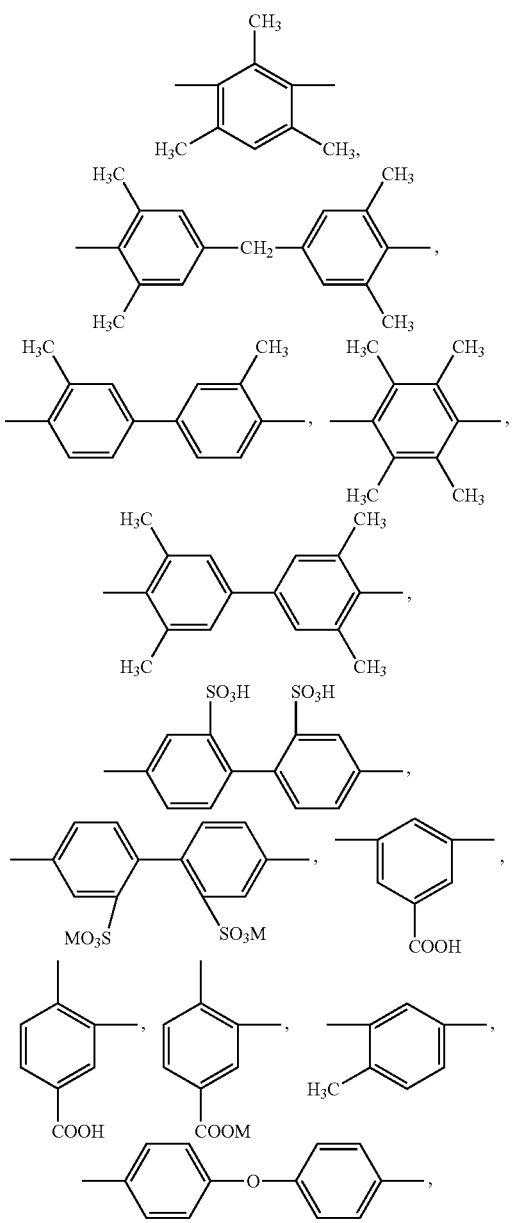

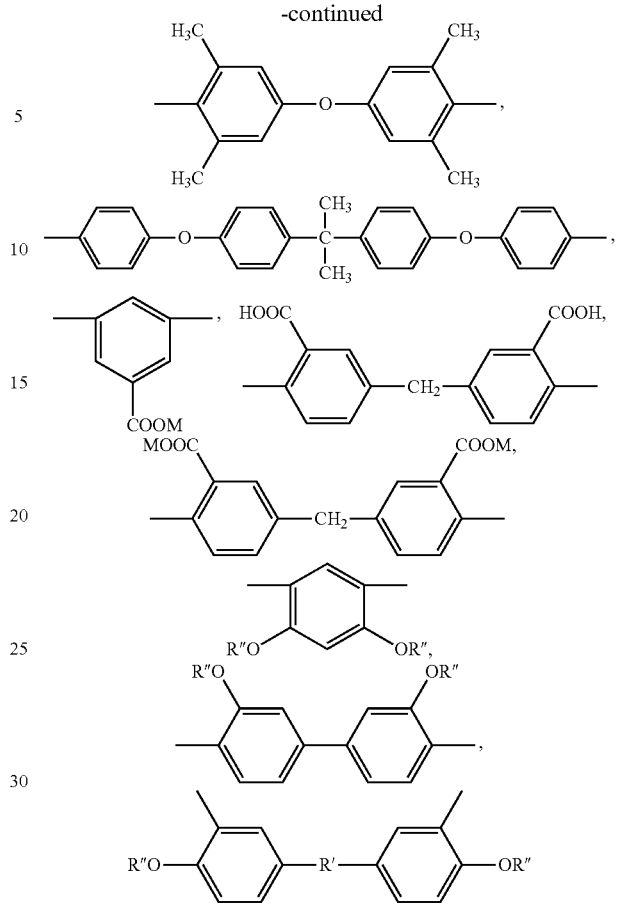

and mixtures thereof, and —R'— is selected from the group consisting of

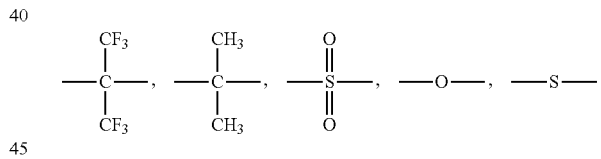

and mixtures thereof, and —R"— is selected from the group consisting of —H, COCH$_3$, and mixtures thereof, and M is selected from silver (I) cation or copper (I) cation; wherein n and m are independent integers from 2 to 500; and wherein n/m is in a range of 1:0 to 1:10, and preferably n/m is in a range of 1:0 to 1:5.

Preferably, $X_1$ and $X_2$ are selected from the group consisting of

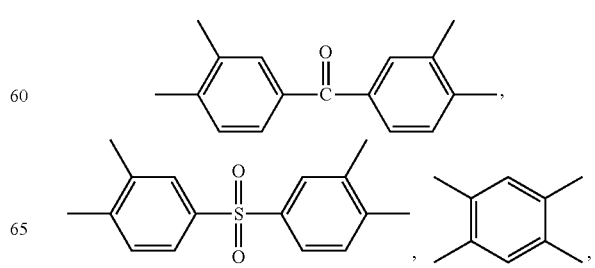

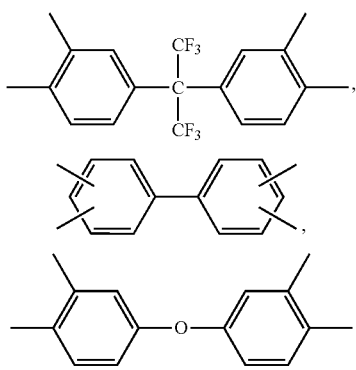

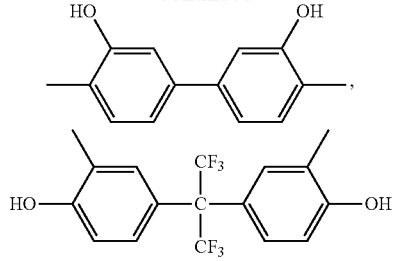

and mixtures thereof, and wherein X1 and X2 may be the same or different from each other; preferably $Y_1$—COOM is selected from the group consisting of

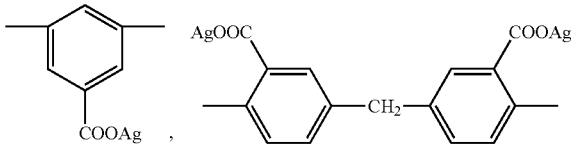

and mixtures thereof; preferably Y2 is selected from the group consisting of

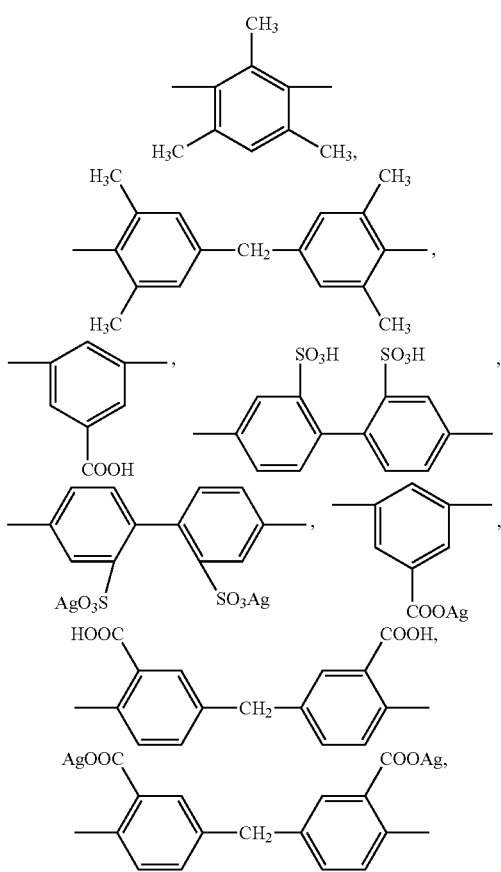

and mixtures thereof.

The stable high performance facilitated transport membrane described in U.S. application Ser. No. 15/600,300 comprising an asymmetric integrally-skinned polymeric membrane wherein the pores on a relatively porous, thin, dense skin layer of the membrane comprises a hydrophilic polymer, a metal salt or a mixture of a metal salt and hydrogen peroxide, wherein said asymmetric integrally-skinned polymeric membrane comprises a relatively porous, thin, dense skin layer as characterized by a $CO_2$ permeance of at least 200 GPU and a $CO_2$ over $CH_4$ selectivity between 1.1 and 10 at 50° C. under 50-1000 psig, 10% $CO_2$/90% $CH_4$ mixed gas feed pressure can be used as the membranes in the first membrane module, the third membrane module, and the rectification membrane module in the present invention. The stable high performance facilitated transport membrane described in U.S. application Ser. No. 15/600,300 used as the membranes in the first membrane module, the third membrane module, and the rectification membrane module in the present invention comprises a polymer selected from a group consisting of a polyimide, a blend of two or more different polyimides, and a blend of a polyimide and a polyethersulfone and wherein the the polyimide can be selected from the group consisting of poly(2,2'-bis-(3,4-dicarboxyphenyl)hexafluoropropane dianhydride-3,3',5,5'-tetramethyl-4,4'-methylene dianiline) polyimide derived from a polycondensation reaction of 2,2'-bis-(3,4-dicarboxyphenyl)hexafluoropropane dianhydride (6FDA) with 3,3',5,5'-tetramethyl-4,4'-methylene dianiline (TMMDA), poly(3,3',4,4'-diphenylsulfone tetracarboxylic dianhydride-3,3',5,5'-tetramethyl-4,4'-methylene dianiline) polyimide derived from the polycondensation reaction of 3,3',4,4'-diphenylsulfone tetracarboxylic dianhydride (DSDA) with TMMDA, poly(3,3',4,4'-benzophenone tetracarboxylic dianhydride-pyromellitic dianhydride-3,3',5,5'-tetramethyl-4,4'-methylene dianiline) polyimide derived from the polycondensation reaction of a mixture of 3,3',4,4'-benzophenone tetracarboxylic dianhydride (BTDA) and pyromellitic dianhydride (PMDA) with TMMDA, poly(3,3',4,4'-benzophenone tetracarboxylic dianhydride-pyromellitic dianhydride-2,4,6-trimethyl-1,3-phenylenediamine) polyimide derived from the polycondensation reaction of a mixture of BTDA and PMDA with 2,4,6-trimethyl-1,3-phenylenediamine (TMPDA), poly(3,3',4,4'-benzophenone tetracarboxylic dianhydride-pyromellitic dianhydride-2,4,6-trimethyl-1,3-phenylenediamine-2,4-toluenediamine) polyimide derived from the polycondensation reaction of a mixture of BTDA and PMDA with a mixture of TMPDA and 2,4-toluenediamine (2,4-TDA), and poly(3,3',4,4'-diphenylsulfone tetracarboxylic dianhydride-3,3',5,5'-tetramethyl-4,4'-methylene dianiline-4,4'-diamino-2-methylazobenzene) polyimide derived from the polycondensation reaction of DSDA with a mixture of TMMDA and 4,4'-diamino-2-methylazobenzene (DAMAB).

The membranes used in the first membrane module, the third membrane module, and the rectification membrane module may comprise a co-cast thin film composite flat sheet membrane comprising an asymmetric porous non-selective support layer and an asymmetric integrally skinned polyimide-containing selective layer on top of said asymmetric porous non-selective support layer wherein said asymmetric porous non-selective support layer comprises a non-polyimide polymer or a mixture of a non-polyimide polymer and a polyimide polymer and wherein the weight ratio of said non-polyimide polymer to said polyimide polymer in said mixture is in a range of 20:1 to 2:1 as described in U.S. application Ser. No. 15/599,258.

The second membrane module and the fourth membrane module may comprise the same or similar functioning membranes that comprise a membrane as recently described in U.S. application Ser. No. 15/598,168 filed May 17, 2017; U.S. application Ser. No. 15/615,134 filed Jun. 6, 2017; and U.S. Provisional Application No. 62/549,820 filed Aug. 24, 2017 incorporated herein in their entireties.

The high selectivity facilitated transport membrane disclosed in U.S. application Ser. No. 15/598,168 comprising a relatively hydrophilic, very small pore, nanoporous support membrane, a hydrophilic polymer inside the very small nanopores on the skin layer surface of the support membrane, a thin, nonporous, hydrophilic polymer layer coated on the surface of the support membrane, and metal salts incorporated in the hydrophilic polymer layer coated on the surface of the support membrane and the hydrophilic polymer inside the very small nanopores can be used as the membranes in the second membrane module and the fourth membrane module described in the present invention. The relatively hydrophilic, very small pore, nanoporous support membrane used for the preparation of the new facilitated transport membrane comprising a relatively hydrophilic, very small pore, nanoporous support membrane, a hydrophilic polymer inside the very small nanopores on the surface of the support membrane, a thin, nonporous, hydrophilic polymer layer coated on the surface of said support membrane, and metal salts incorporated in the hydrophilic polymer layer coated on the surface of the support membrane and said hydrophilic polymer inside the very small nanopores disclosed in the present invention comprises a relatively hydrophilic polymer selected from a group consisting of, but is not limited to, polyethersulfone (PES), a blend of PES and polyimide, cellulose acetate, cellulose triacetate, and a blend of cellulose acetate and cellulose triacetate. The relatively hydrophilic, very small pore, nanoporous support membrane described in the current invention has an average pore diameter of less than 10 nm on the membrane skin layer surface. The relatively hydrophilic, very small pore, nanoporous support membrane described in the current invention can be either asymmetric integrally skinned membrane or thin film composite (TFC) membrane with either flat sheet (spiral wound) or hollow fiber geometry.

The hydrophilic polymer inside the very small nanopores on the surface of the relatively hydrophilic, very small pore, nanoporous support membrane of the facilitated transport membrane described in U.S. application Ser. No. 15/598,168 can be selected from, but is not limited to, a group of hydrophilic polymers containing chitosan, sodium carboxylmethyl-chitosan, carboxylmethyl-chitosan, hyaluronic acid, sodium hyaluronate, carbopol, polycarbophil calcium, poly(acrylic acid) (PAA), poly(methacrylic acid) (PMA), sodium alginate, alginic acid, poly(vinyl alcohol) (PVA), poly(ethylene oxide) (PEO), poly(ethylene glycol) (PEG), poly(vinylpyrrolidone) (PVP), gelatin, carrageenan, sodium lignosulfonate, and mixtures thereof.

The metal salts incorporated in the hydrophilic polymer layer coated on the surface of said support membrane and the hydrophilic polymer inside the very small nanopores of the facilitated transport membrane described in Ser. No. 15/598,168 are preferred to be selected from silver salts or copper salts, such as silver(I) nitrate or copper(I) chloride.

The dried, relatively hydrophilic, very small pore, nanoporous support membrane comprising hydrophilic polymers inside the very small nanopores on the membrane surface described in U.S. application Ser. No. 15/598,168 has carbon dioxide permeance of 800-10,000 GPU and no carbon dioxide/methane selectivity at 50° C. under 30-100 psig 10% $CO_2$/90% $CH_4$ mixed gas feed pressure.

The new facilitated transport membrane disclosed in U.S. application Ser. No. 15/615,134 comprising a nanoporous polyethersulfone/polyvinylpyrrolidone blend support membrane, a hydrophilic polymer inside nanopores of said support membrane, a hydrophilic polymer coating layer on a surface of the support membrane and metal salts in said hydrophilic polymer coating layer and in said hydrophilic polymer inside said nanopores of said support membrane can also be used as the membranes in the second membrane module and the fourth membrane module described in the present invention.

The membrane disclosed in U.S. Provisional Application No. 62/549,820 comprising a polyethersulfone/polyethylene oxide-polysilsesquioxane blend support membrane comprising a polyethylene oxide-polysilsesquioxane polymer and a polyethersulfone polymer; a hydrophilic polymer inside the pores on the skin layer surface of the polyethersulfone/polyethylene oxide-polysilsesquioxane blend support membrane; a hydrophilic polymer coated on the skin layer surface of the polyethersulfone/polyethylene oxide-polysilsesquioxane blend support membrane, and metal salts incorporated in the hydrophilic polymer coating layer and the the skin layer surface pores of the polyethersulfone/polyethylene oxide-polysilsesquioxane blend support membrane can also be used as the membranes in the second membrane module and the fourth membrane module described in the present invention.

Figure 3:
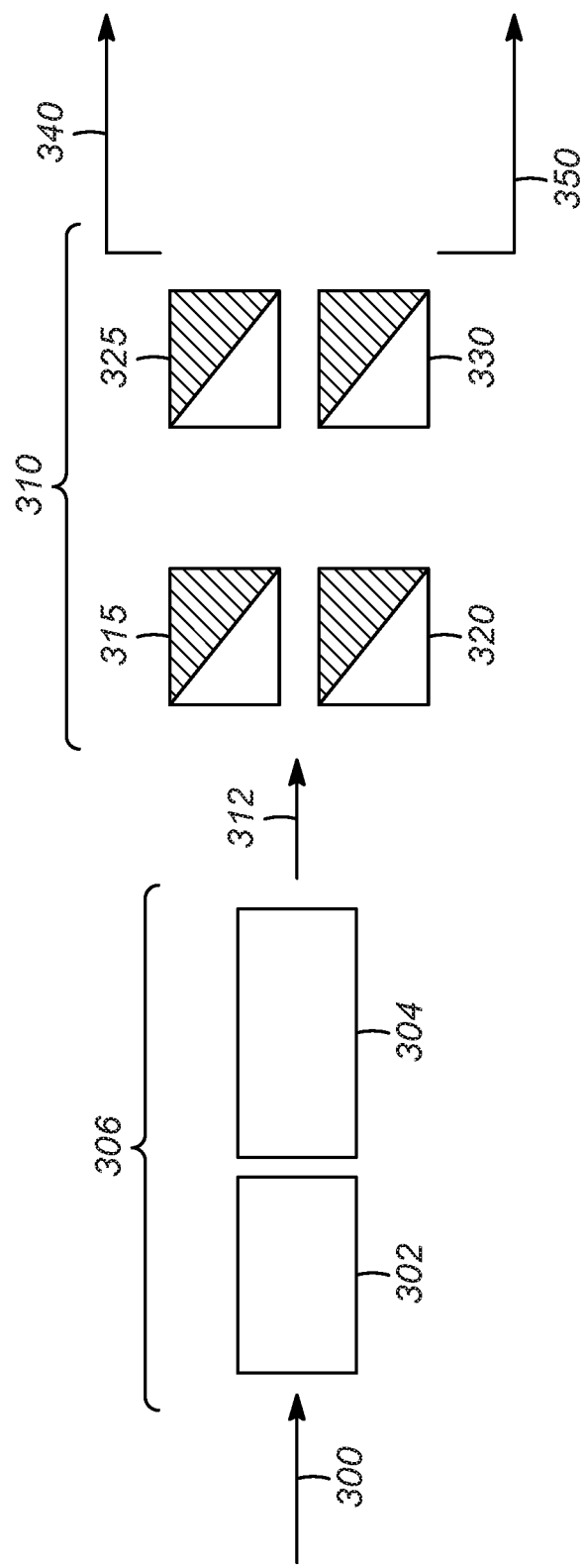
FIG. 3 is a block flow diagram that shows a pretreatment zone to remove impurities as well as a four membrane module separation zone.

In FIG. 1 is shown a modular membrane train that is capable of producing 40 KMTA propylene. All concentrations that are discussed are regarding mol % propylene. In this example, the hydrocarbon feed 10 is 65 mol % propylene with a total volume of hydrocarbon processed of 66.76 KMTA feed that has been treated (as shown in FIG. 3) to remove impurities that may interfere with the function of the membranes or otherwise are undesirable. A flow 12 of water vapor is shown being added to the hydrocarbon feed 10 which has been vaporized and which then contacts a first membrane module 14 (also referred to as a sub-module herein) that in this example has 100 membrane elements with high propylene permeance (about 160-330 GPU, 1 GPU=$10^{-6}$ $cm^3$ (STP)/$cm^2$·sec·cmHg) and moderately low propylene/propane selectivity (about 30-50) for the hydrocarbon to contact and to produce a first permeate stream 15 having 86.4 mol % propylene and a first non-permeate stream 38 that has 17.9 mol % propylene. First permeate stream 15 passes through a mixer 16 with the now combined first permeate stream 18 having 86.7 mol % propylene to pass through compressor 20 to produce first compressed stream 22 having a water vapor stream 23 added before the stream passes through heat exchanger 24 to provide a stream 25 to have the temperature adjusted to the required temperature and then contact membrane elements having a higher selectivity (about 250-1100, or preferably 300-950) within membrane module 26 to produce a second permeate stream 28 that is compressed by compressor 30 to produce compressed stream 32 that is shown passing through heat exchanger 34 to result in propylene product stream 36 that is 99.5 mol % propylene with 41.08 KMTA produced. First non-permeate stream 38 passes through mixer 40 to become a stream 42 having 19.5 mol % propylene to pass through a third compressor 44 with compressed stream 46 having a water vapor stream 48 added before the stream passes through heat exchanger 50 with stream 52 contacting third membrane module 54 that contains 120 membrane elements that are of relatively low selectivity (high propylene permeance of about 160-330 GPU and moderately low propylene/propane selectivity of about 30-50) compared to the second membrane module 26. A permeate stream 62 has 38.4 mol % propylene and passes through mixer 64 to stream 66, compressor 68 to produce stream 70 with water vapor stream 72 added before stream 70 passes through heat exchanger 74 to produce stream 76 to contact $4^{th}$ membrane module 82 having 80 membrane elements that are of a higher selectivity that is comparable to second membrane module 26. Fourth permeate stream 84 that is 88.4 mol % propylene is sent back to mixer 16 to be combined with first permeate stream 15. Fourth non-permeate stream 80 that is 21.3 mol % propylene is sent to mixer 40 to be combined with first non-permeate stream 38. A third non-permeate stream 56 is shown passing through heat exchanger 58 with a mostly propane stream 60 having 7.5 mol % propylene with about 25.72 KMTA produced. Modifications of this flow scheme may be made, provided that there is produced a product stream that is in the target range of about 99.3-99.8 mol % propylene. Note that though not shown in the figure, the propylene product is typically dried with regenerable adsorbents for the final dried product.

FIG. 2 shows an alternate embodiment that provides for the addition of a propylene-containing stream from a propane dehydrogenation process that has a significantly lower proportion propylene compared to the FCC stream. In this example, the hydrocarbon feed 100 is 65 mol % propylene with a total volume of hydrocarbon processed of 66.76 KMTA feed that has been treated (as shown in FIG. 3) to remove impurities that may interfere with the function of the membranes or otherwise are undesirable. A flow 101 of water vapor is shown being added to the hydrocarbon feed 100 which has been vaporized and which then contacts a first membrane module 102 (also referred to as a sub-module herein) that in this example has 118 membrane elements with high propylene permeance of about 160-330 GPU and moderately low propylene/propane selectivity of about 30-50 for the hydrocarbon to contact and to produce a first permeate stream 104 having 86.2 mol % propylene and a first non-permeate stream 105 that has 17.2 mol % propylene. First permeate stream 104 passes through a mixer 106 with the now combined first permeate stream 108 having 86.3 mol % propylene to pass through compressor 110 to produce first compressed stream 122 having a water vapor stream 114 added before the stream passes through heat exchanger 116 to stream 118 to have the temperature adjusted to the required temperature and then contact membrane elements having a higher selectivity (about 250-1100, or preferably 300-950) within $2^{nd}$ membrane module 120 with 80 membrane elements to produce a second permeate stream 124 that is compressed by compressor 126 to produce compressed stream 128 that is shown passing through heat exchanger 130 to result in propylene product stream 132 that is 99.5 mol % propylene with 50.61 KMTA produced from the original two feeds. First non-permeate stream 105 passes through mixer 158 to become a stream 160 having 19.2 mol % propylene to pass through a third compressor 162 with compressed stream 164 having a water vapor stream 166 added before the stream passes through heat exchanger 168 with stream 169 contacting third membrane module 172 that contains 240 membrane elements that are of relatively low selectivity compared to second membrane module 120. A $3^{rd}$ permeate stream 180 has 37.4 mol % propylene and passes through mixer 182 to stream 184 to compressor 186 to produce stream 188 with water vapor stream 190 added before stream 188 passes through heat exchanger 192 to produce stream 194 to contact $4^{th}$ membrane module 196 having 135 membrane elements that are of a higher selectivity that is comparable to second membrane module 120. Fourth permeate stream 200 that is 86.8 mol % propylene is sent back to mixer 106 to be combined with first permeate stream 104. Fourth non-permeate stream 198 that is 21.0 mol % propylene is sent to mixer 158 to be combined with first non-permeate stream 105. A third non-permeate stream 174 is shown passing through heat exchanger 176 with a mostly propane stream 178 having 7.1 mol % propylene with about 48.3 KMTA produced. The main difference from FIG. 1 is that a second hydrocarbon stream 140 that is 35 mol % propylene is sent to an initial membrane module 144 with water vapor first injected at 142. An initial permeate stream 146 that is 68 mol % propylene is sent to compressor 148 to stream 152, heat exchanger 150 to stream 154 to be combined with hydrocarbon stream 100. An initial non-permeate stream 156 is sent to mixer 158 to be combined with first non-permeate stream 105 and $4^{th}$ non-permeate stream 198. Modifications of this flow scheme may be made, provided that there is produced a product stream that is in the target range of about 99.3-99.8 mol % propylene. Note that the propylene product is typically dried with regenerable adsorbents for the final dried product.

FIG. 3 shows a block diagram of the process that is shown in detail in FIG. 1 with the addition of a pretreatment step. A feed that contains olefins and paraffins that is either an ethane/ethylene or propane/propylene plus impurities stream 300 is shown passing through a pretreatment zone 306 that includes an adsorption zone 302 and a selective hydrogenation zone 304 to produce a treated feed 312 that passes through separation zone 310 that is shown with four membrane modules 315, 320, 325 and 330. An olefin product 340 that contains 99.2 to 99.8 mol % olefin is produced. A paraffin product 350 contains 91-96 mol % paraffin.

Figure 4:
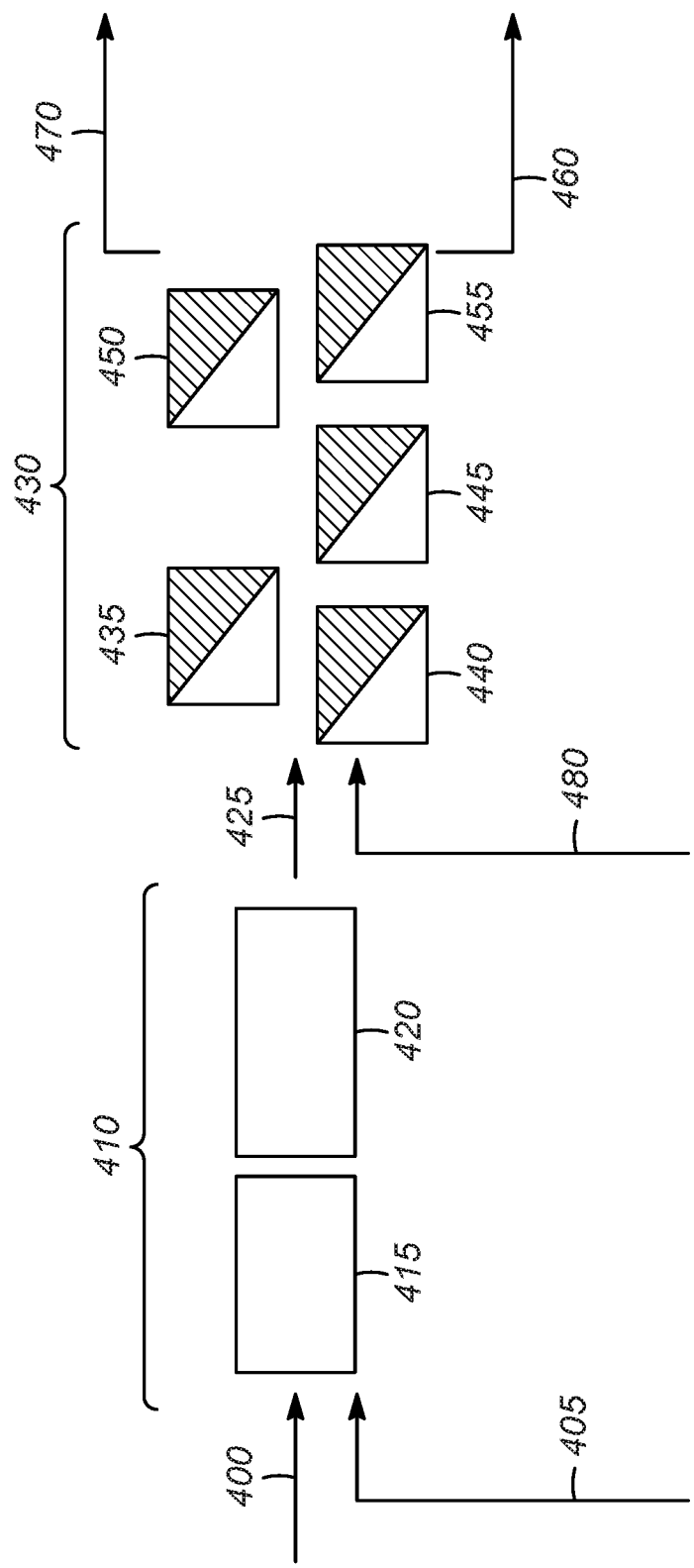
FIG. 4 is block flow diagram for processing two different hydrocarbon feed streams with a pretreatment zone and a five membrane module separation zone.

FIG. 4 is a block flow diagram for the process shown in detail in FIG. 2. An ethane/ethylene or propane/propylene stream plus impurities stream 400 is shown passing through a pretreatment zone 410 that includes an adsorption zone 415 and a selective hydrogenation zone 420 to produce a treated feed 425 that passes through separation zone 430 that is shown with five membrane modules 435, 440, 445, 450 and 455. An olefin product 470 that contains 99.2 to 99.8 mol % olefin is produced. A paraffin product 460 is 91-96 mol % paraffin. Also shown are untreated feed stream 405 from a different source that needs to be treated in pretreatment zone 410 as well as treated feed stream 480 that is also from a different source than stream 400.

Specific Embodiments

While the following is described in conjunction with specific embodiments, it will be understood that this description is intended to illustrate and not limit the scope of the preceding description and the appended claims.

A first embodiment of the invention is a process to separate a hydrocarbon stream comprising a mixture of light olefins and light paraffins, the process comprising (a) pre-treating the hydrocarbon stream to remove impurities to produce a treated hydrocarbon stream; (b) vaporizing the treated hydrocarbon stream to produce a gaseous treated hydrocarbon stream; (c) adding water to the gaseous treated hydrocarbon stream; (d) sending the gaseous treated hydrocarbon stream with water to a first membrane module comprising a multiplicity of membrane units comprising membranes having a higher permeance and a lower selectivity than the membranes in the membrane units in a second membrane module to produce a first permeate stream comprising a higher concentration of light olefins than the gaseous treated hydrocarbon stream and a first non-permeate stream comprising a higher concentration of light paraffins than the gaseous treated hydrocarbon stream; (e) sending the first permeate stream to the second membrane module comprising membrane units comprising membranes having a higher selectivity than the membranes in the membrane units in the first membrane module to produce a second permeate stream comprising at least 99% light olefins and a second non-permeate stream comprising a lower concentration of light olefins than the second permeate stream; (f) sending the first non-permeate stream to a third membrane module comprising membrane units comprising membranes having a higher permeance and lower selectivity than the membranes in the membrane units in the second membrane module to produce a third permeate stream comprising a higher concentration of light olefin than the first non-permeate stream and a non-permeate stream comprising a majority concentration of paraffin; (g) sending the third permeate stream to a fourth membrane module comprising membrane units comprising membranes having a higher selectivity than the membranes in the first membrane units in the first membrane module to produce a fourth permeate stream comprising a higher concentration of light olefin than the third permeate stream; and (h) combining the fourth permeate stream with the first permeate stream. An embodiment of the invention is one, any or all of prior embodiments in this paragraph up through the first embodiment in this paragraph wherein the second permeate stream comprises 99.3 to 99.9% propylene. An embodiment of the invention is one, any or all of prior embodiments in this paragraph up through the first embodiment in this paragraph wherein the hydrocarbon stream comprises a hydrocarbon stream from one or more processes selected from the group consisting of thermal steam crackers, fluid catalytic cracking and propane dehydrogenation. An embodiment of the invention is one, any or all of prior embodiments in this paragraph up through the first embodiment in this paragraph wherein water is added to the first permeate stream, the first non-permeate stream and the third permeate stream before each of the streams enters a membrane module. An embodiment of the invention is one, any or all of prior embodiments in this paragraph up through the first embodiment in this paragraph wherein the membrane units in the first membrane module and the third membrane module comprise a stable high performance facilitated transport membrane comprising an asymmetric integrally-skinned polymeric membrane wherein the pores on a relatively porous, thin, dense skin layer of the membrane comprises a hydrophilic polymer, a metal salt or a mixture of a metal salt and hydrogen peroxide, wherein the asymmetric integrally-skinned polymeric membrane comprises a relatively porous, thin, dense skin layer as characterized by a $CO_2$ permeance of at least 200 GPU and a $CO_2$ over $CH_4$ selectivity between 1.1 and 10 at 50° C. under 50-1000 psig, 10% $CO_2$/90% $CH_4$ mixed gas feed pressure. An embodiment of the invention is one, any or all of prior embodiments in this paragraph up through the first embodiment in this paragraph wherein the membrane units in the first membrane module and the third membrane module comprise a stable high performance facilitated transport membrane comprising a co-cast thin film composite flat sheet membrane comprising an asymmetric porous non-selective support layer and an asymmetric integrally skinned polyimide-containing selective layer on top of the asymmetric porous non-selective support layer wherein the pores on the surface of the asymmetric integrally skinned polyimide-containing selective layer comprises a hydrophilic polymer, a metal salt or a mixture of a metal salt and hydrogen peroxide. An embodiment of the invention is one, any or all of prior embodiments in this paragraph up through the first embodiment in this paragraph wherein the membrane units in the first membrane module and the third membrane module comprise a facilitated transport membrane comprising a carboxylic acid functional group containing polyimide wherein the carboxylic acid functional groups are ion-exchanged or chelated with metal cations such as silver (I) or copper (I) cations. An embodiment of the invention is one, any or all of prior embodiments in this paragraph up through the first embodiment in this paragraph wherein the membrane units in the second membrane module and the fourth membrane module comprise a high selectivity facilitated transport membrane comprising a relatively hydrophilic, very small pore, nanoporous support membrane, a hydrophilic polymer inside the very small nanopores on the skin layer surface of the support membrane, a thin, nonporous, hydrophilic polymer layer coated on the surface of the support membrane, and metal salts incorporated in the hydrophilic polymer layer coated on the surface of the support membrane and the hydrophilic polymer inside the very small nanopores. An embodiment of the invention is one, any or all of prior embodiments in this paragraph up through the first embodiment in this paragraph wherein the membrane units in the second membrane module and the fourth membrane module comprise a polyethersulfone/polyethylene oxide-polysilsesquioxane blend support membrane comprising a polyethylene oxide-polysilsesquioxane polymer and a polyethersulfone polymer, a hydrophilic polymer inside the pores on the skin layer surface of the polyethersulfone/polyethylene oxide-polysilsesquioxane blend support membrane, a hydrophilic polymer coated on the skin layer surface of the polyethersulfone/polyethylene oxide-polysilsesquioxane blend support membrane, and metal salts incorporated in the hydrophilic polymer coating layer and the the skin layer surface pores of the polyethersulfone/polyethylene oxide-polysilsesquioxane blend support membrane. An embodiment of the invention is one, any or all of prior embodiments in this paragraph up through the first embodiment in this paragraph wherein at least a portion of the hydrocarbon stream comprises a feed from a propane dehydrogenation reaction comprising about 30-40% propylene, the process comprising an initial rectification membrane module comprising membrane units comprising membranes having higher permeance and lower selectivity than the membrane units in the second membrane module to produce a rectification permeate stream comprising about 55-80% light olefin. An embodiment of the invention is one, any or all of prior embodiments in this paragraph up through the first embodiment in this paragraph wherein rectification permeate stream is added to the hydrocarbon stream before the hydrocarbon stream is sent to the first membrane module. An embodiment of the invention is one, any or all of prior embodiments in this paragraph up through the first embodiment in this paragraph wherein the rectification membrane module comprises membrane units comprising membranes same as the membranes in the membrane units in the first membrane module or the third membrane module. An embodiment of the invention is one, any or all of prior embodiments in this paragraph up through the first embodiment in this paragraph wherein after the water vapor is added to the permeate streams and the non-permeate stream, the permeate streams and the non-permeate stream has from 10% to 100% humidity. An embodiment of the invention is one, any or all of prior embodiments in this paragraph up through the first embodiment in this paragraph wherein the permeate stream has from 60% to 90% humidity. An embodiment of the invention is one, any or all of prior embodiments in this paragraph up through the first embodiment in this paragraph wherein the impurities are selected from the group consisting of arsine, phosphine, sulfur compounds, acetylenes, and dienes. An embodiment of the invention is one, any or all of prior embodiments in this paragraph up through the first embodiment in this paragraph wherein the hydrocarbon stream is at a pressure from about 100 to 500 psig before entering a membrane module. An embodiment of the invention is one, any or all of prior embodiments in this paragraph up through the first embodiment in this paragraph wherein the hydrocarbon stream is at a temperature from about 30° to 90° C. An embodiment of the invention is one, any or all of prior embodiments in this paragraph up through the first embodiment in this paragraph wherein the second non-permeate stream is mixed with the third permeate stream and then a combined third permeate stream is sent to the fourth membrane module. An embodiment of the invention is one, any or all of prior embodiments in this paragraph up through the first embodiment in this paragraph wherein the light olefins are ethylene, propylene or mixtures thereof.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process to separate a hydrocarbon stream comprising a mixture of light olefins and light paraffins, said process comprising:
 (a) pretreating said hydrocarbon stream to remove impurities to produce a treated hydrocarbon stream;
 (b) vaporizing said treated hydrocarbon stream to produce a gaseous treated hydrocarbon stream;
 (c) adding water to said gaseous treated hydrocarbon stream;
 (d) sending said gaseous treated hydrocarbon stream with water vapor to a first membrane module comprising a multiplicity of membrane units comprising membranes having a higher permeance and a lower selectivity than the membranes in the membrane units in a second membrane module to produce a first permeate stream comprising a higher concentration of light olefins than said gaseous treated hydrocarbon stream and a first non-permeate stream comprising a higher concentration of light paraffins than said gaseous treated hydrocarbon stream;
 (e) sending said first permeate stream to said second membrane module comprising membrane units comprising membranes having a higher selectivity than said membranes in said membrane units in said first membrane module to produce a second permeate stream comprising at least 99% light olefins and a second non-permeate stream comprising a lower concentration of light olefins than said second permeate stream;
 (f) sending said first non-permeate stream to a third membrane module comprising membrane units comprising membranes having a higher permeance and lower selectivity than said membranes in said membrane units in said second membrane module to produce a third permeate stream comprising a higher concentration of light olefin than said first non-permeate stream and a non-permeate stream comprising a majority concentration of paraffin;
 (g) sending said third permeate stream to a fourth membrane module comprising membrane units comprising membranes having a higher selectivity than said membranes in said first membrane units in said first membrane module to produce a fourth permeate stream comprising a higher concentration of light olefin than said third permeate stream; and
 (h) combining said fourth permeate stream with said first permeate stream, wherein said membrane units in said first membrane module and said third membrane module comprise a stable high performance facilitated transport membrane comprising a co-cast thin film composite flat sheet membrane comprising an asymmetric porous non-selective support layer and an asymmetric integrally skinned polyimide-containing selective layer on top of said asymmetric porous non-selective support layer wherein pores on the surface of said asymmetric integrally skinned polyimide-containing selective layer comprises a hydrophilic polymer, a metal salt or a mixture of a metal salt and hydrogen peroxide.

2. The process of claim 1 wherein said second permeate stream comprises 99.3 to 99.9% propylene.

3. The process of claim 1 wherein said hydrocarbon stream comprises a hydrocarbon stream from one or more processes selected from the group consisting of fluid catalytic cracking and propane dehydrogenation.

4. The process of claim 1 wherein water is added to each permeate and non-permeate stream sent to a membrane module.

5. The process of claim 1 wherein said membrane units in said first membrane module and said third membrane module comprise a stable high performance facilitated transport membrane comprising an asymmetric integrally-skinned polymeric membrane wherein the pores on a porous, thin, dense skin layer of the membrane comprises a hydrophilic polymer, a metal salt or a mixture of a metal salt and hydrogen peroxide, wherein said asymmetric integrally skinned polymeric membrane comprises a porous, thin, dense skin layer as characterized by a $CO_2$ permeance of at least 200 GPU and a $CO_2$ over $CH_4$ selectivity between 1.1 and 10 at 50° C. under 345 to 6895 kPa (50 to 1000 psig), 10% $CO_2$/90% $CH_4$ mixed gas feed pressure.

6. The process of claim 1 wherein said membrane units in said first membrane module and said third membrane module comprise a facilitated transport membrane comprising a carboxylic acid functional group containing polyimide wherein the carboxylic acid functional groups are ion-exchanged or chelated with silver (I) or copper (I) cations.

7. The process of claim 1 wherein said hydrocarbon stream comprises a feed from a propane dehydrogenation reaction which is passed to an initial rectification membrane module, said feed comprising about 30-40% propylene, said initial rectification membrane module further comprising membrane units comprising membranes having higher permeance and lower selectivity than said membrane units in said second membrane module to produce a rectification permeate stream comprising about 55-80% light olefin.

8. The process of claim 7 wherein rectification permeate stream is added to said hydrocarbon stream before said hydrocarbon stream is sent to said first membrane module.

9. The process of claim 7 wherein said rectification membrane module comprises membrane units comprising membranes which are the same as the membranes in the first or third membrane module.

10. The process of claim 4 wherein after water addition each permeate and non-permeate stream has from 10 to 100% humidity.

11. The process of claim 10 wherein each permeate stream has from 60% to 90% humidity.

12. The process of claim 1 wherein said impurities are selected from the group consisting of arsine, phosphine, sulfur compounds, acetylenes, and dienes.

13. The process of claim 1 wherein said hydrocarbon stream is at a pressure from about 690 to 3447 kPa (100 to 500 psig) before entering a membrane module.

14. The process of claim 1 wherein said hydrocarbon stream is at a temperature from about 30 to 90° C.

15. The process of claim 1 wherein said second non-permeate stream is mixed with said third permeate stream and then a combined third permeate stream is sent to said fourth membrane module.

16. The process of claim 1 wherein said light olefins are ethylene, propylene or mixtures thereof.

17. A process to separate a hydrocarbon stream comprising a mixture of light olefins and light paraffins, said process comprising:
 (a) pretreating said hydrocarbon stream to remove impurities to produce a treated hydrocarbon stream;
 (b) vaporizing said treated hydrocarbon stream to produce a gaseous treated hydrocarbon stream;
 (c) adding water to said gaseous treated hydrocarbon stream;
 (d) sending said gaseous treated hydrocarbon stream with water vapor to a first membrane module comprising a multiplicity of membrane units comprising membranes having a higher permeance and a lower selectivity than the membranes in the membrane units in a second membrane module to produce a first permeate stream comprising a higher concentration of light olefins than said gaseous treated hydrocarbon stream and a first non-permeate stream comprising a higher concentration of light paraffins than said gaseous treated hydrocarbon stream;
 (e) sending said first permeate stream to said second membrane module comprising membrane units comprising membranes having a higher selectivity than said membranes in said membrane units in said first membrane module to produce a second permeate stream comprising at least 99% light olefins and a second non-permeate stream comprising a lower concentration of light olefins than said second permeate stream;
 (f) sending said first non-permeate stream to a third membrane module comprising membrane units comprising membranes having a higher permeance and lower selectivity than said membranes in said membrane units in said second membrane module to produce a third permeate stream comprising a higher concentration of light olefin than said first non-permeate stream and a non-permeate stream comprising a majority concentration of paraffin;
 (g) sending said third permeate stream to a fourth membrane module comprising membrane units comprising membranes having a higher selectivity than said membranes in said first membrane units in said first membrane module to produce a fourth permeate stream comprising a higher concentration of light olefin than said third permeate stream; and
 (h) combining said fourth permeate stream with said first permeate stream,
  wherein said membrane units in said second membrane module and said fourth membrane module comprise a high selectivity facilitated transport membrane comprising a hydrophilic, nanoporous support membrane, a hydrophilic polymer inside the nanopores on a skin layer surface of the support membrane, a thin, nonporous, hydrophilic polymer layer coated on the surface of the support membrane, and metal salts incorporated in the hydrophilic polymer layer coated on the surface of the support membrane and the hydrophilic polymer inside the nanopores.

18. The process of claim 17 wherein said membrane units in said second membrane module and said fourth membrane module comprise a polyethersulfone/polyethylene oxide-polysilsesquioxane blend support membrane comprising a polyethylene oxide-polysilsesquioxane polymer and a polyethersulfone polymer, a hydrophilic polymer inside the nanopores on the skin layer surface of the polyethersulfone/polyethylene oxide-polysilsesquioxane blend support membrane, a hydrophilic polymer coated on the skin layer surface of the polyethersulfone/polyethylene oxide-polysilsesquioxane blend support membrane, and metal salts incorporated in the hydrophilic polymer coating layer and the skin layer surface pores of the polyethersulfone/polyethylene oxide-polysilsesquioxane blend support membrane.

19. The process of claim 17 wherein said membrane units in said first membrane module and said third membrane module comprise a stable high performance facilitated transport membrane comprising a co-cast thin film composite flat sheet membrane comprising an asymmetric porous non-selective support layer and an asymmetric integrally skinned polyimide-containing selective layer on top of said asymmetric porous non-selective support layer wherein pores on the surface of said asymmetric integrally skinned polyimide-containing selective layer comprises a hydrophilic polymer, a metal salt or a mixture of a metal salt and hydrogen peroxide.

* * * * *